United States Patent [19]

Mims, Jr.

[11] 4,220,149
[45] Sep. 2, 1980

[54] ARM SLING

[76] Inventor: Carl C. Mims, Jr., 311 Brainard Ave., Fayetteville, N.C. 28301

[21] Appl. No.: 880,044

[22] Filed: Feb. 22, 1978

[51] Int. Cl.$^2$ ............................................... A61F 5/40
[52] U.S. Cl. ........................................................ 128/94
[58] Field of Search .................................... 128/94, 83

[56] References Cited

U.S. PATENT DOCUMENTS

| 980,464 | 1/1911 | Wermuth | 128/94 |
| 2,875,754 | 3/1959 | Messer | 128/94 |
| 3,433,221 | 3/1969 | Kendall et al. | 128/94 |

FOREIGN PATENT DOCUMENTS

| 661523 | 11/1936 | Fed. Rep. of Germany | 128/94 |
| 482047 | 2/1917 | France | 128/94 |

OTHER PUBLICATIONS

"An Anti-Rotation Arm Sling," The Lancet, Aug. 31, 1963, p. 441.

Primary Examiner—John D. Yasko
Attorney, Agent, or Firm—Mills & Coats

[57] ABSTRACT

In abstract a preferred embodiment of the present invention is an improved arm sling adapted to support the forearm of the wearer in a horizontal orientation. The sling of the present invention comprises a flexible support casing or envelope by which the forearm is supported. The flexible envelope is suspended in place by an adjustable shoulder harness which incorporates a three point support configuration, one each located at the wrist, forearm, and elbow.

7 Claims, 4 Drawing Figures

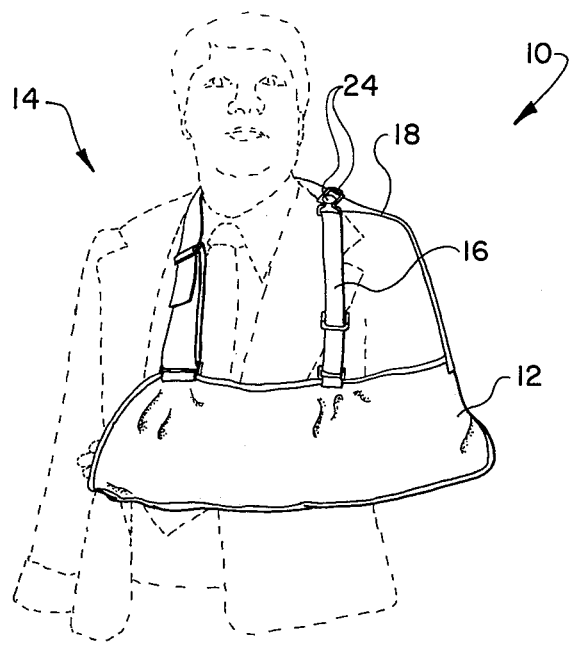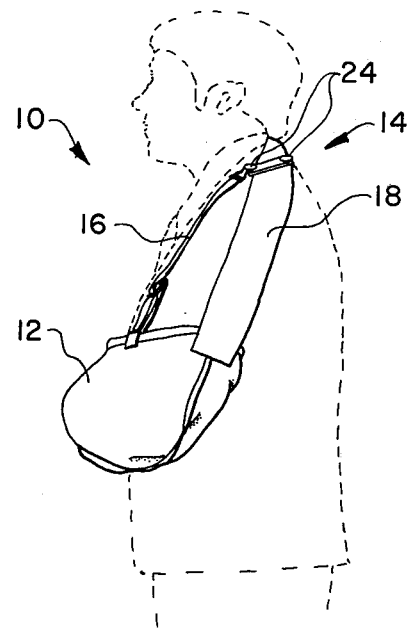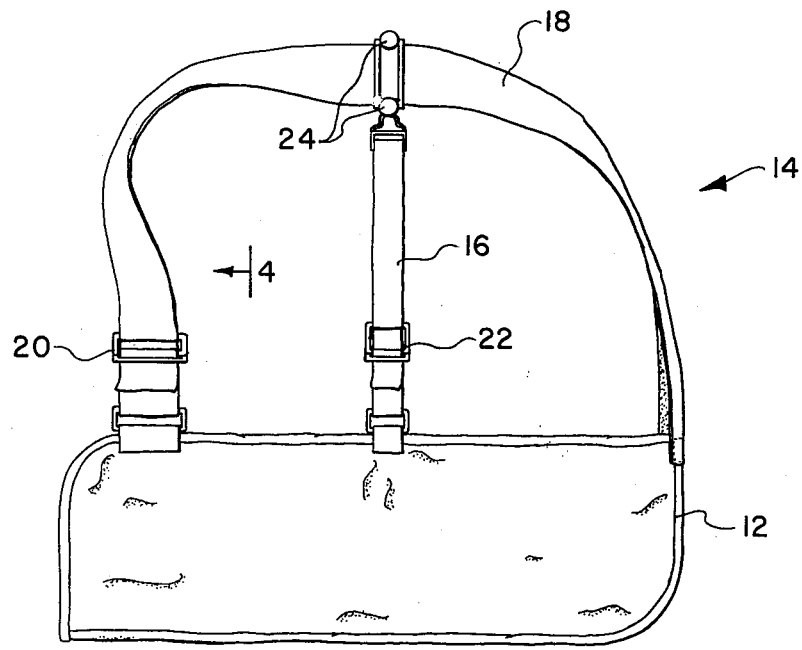

ARM SLING

FIELD OF THE INVENTION

The present invention relates to bandages and more particularly to arm slings.

BACKGROUND OF THE INVENTION

In the past arm slings have generally consisted of a single sheet of material being tied in a loop at the back of the neck and extending downward across the chest. The user's arm would be suspended such that only the forearm was supported thereby allowing the wrist to bend and the hand to hang down. Additionally, all weight from the arm was transferred to the wearer's neck. Obviously, this causes discomfort to the wearer after having worn the sling for only short period of time.

Further improvements have been adapted to the arm sling in the form of a harness to help distrubute the load across the user's back to evenly support the arm. But again, many of these improved slings are cumbersome and lack adjustment capability to function adequately. Additionally, as may be appreciated by one skilled in the art, the conventional sling allows the hand to hang down while the arm is supported. This sometimes causes discomfort to the wearer especially when injury is such that any movement of the hand would cause pain.

SUMMARY OF THE PRESENT INVENTION

After careful study and prolonged observation, the improved arm sling of the present invention has been developed to provide an adjustable arm sling that supports the elbow, forearm, wrist, and hand of the wearer.

In view of the above, it is an object of the present invention to provide an improved arm sling that incorporates an arm support envelope of such an embodiment that the elbow, forearm, wrist, and hand of the wearer may be enclosed therein.

Another object of the present invention is to provide an improved arm sling which incorporates a harness to readily transfer the load of the supported arm and evenly distribute the same across the wearer's shoulder.

A further object of the present invention is to provide an improved arm sling which incorporates a harness to provide support at the elbow, forearm, wrist, and hand of the wearer.

An even further object of the present invention is to provide an improved arm sling that incorporates an adjustable harness whereby the arm of the wearer may be readily supported in a clinically preferred manner.

Another object of the present invention is to provide an improved arm sling that is easy to use, lightweight, and economical to produce.

A further object of the present invention is to provide an improved arm sling that is reversible whereby the same may be adapted to support either the right or left arm of the wearer.

Other objects and advantages of the present invention will become apparent and obvious from a study of the following description and the accompanying drawings which are merely illustrative of such invention.

DESCRIPTION OF THE FIGURES

FIG. 1 is a front elevational view of the improved arm sling of the present invention as it is worn in normal use;

FIG. 2 is a side elevational view of the improved arm sling of the present invention taken to the right of FIG. 1;

FIG. 3 is an enlarged front elevational view of the improved arm sling of the present invention exposing details of the harness and its particular three point attachment to the arm support envelope.

DETAILED DESCRIPTION OF THE DRAWINGS

Figure 4:
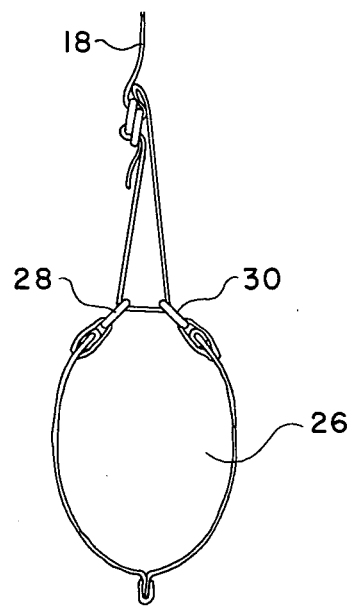
FIG. 4 is a cross sectional view of the improved arm sling of the present invention taken along lines 4—4 of FIG. 3.

With further reference to the drawings, particularly FIGS. 1 and 2, an improved arm sling is shown therein and generally indicated by the numeral 10. Basically arm sling 10 comprises a fabric arm support envelope 12 and a shoulder harness 14. The two are joined at three points whereby equal support may be extended to the wrist, forearm and elbow by envelope 12.

Viewing the harness 14 in greater detail as is illustrated in FIG. 3, the same is shown to include a shoulder strap 16 fixedly secured to arm support envelope 12 about one end and adjustably attached to arm support envelope 12 at its opposite end by buckle 20. A forearm support strap 18 is removably attached by an adjustable fastener 24 about the mid-point of shoulder strap 16 and extends to the mid-point of arm support envelope 12 where the same is adjustably attached by buckle 22.

Viewing arm support envelope 12 in greater detail, the same is shown to have a generally elongated configuration with an arm support cavity 26 disposed therein as illustrated in FIG. 4.

Viewing FIG. 4 which is a cross sectional view of the improved sling of the present invention taken along lines 4—4 of FIG. 3, the particular adjustable attachment of shoulder strap 16 to arm envelope 12 is illustrated. Shoulder strap 16 is shown to extend through two oppositely disposed rings 28 and 30 and attached to the periphery of either side of the arm support cavity thereby causing envelope 12 to support the wearer's arm therein. It will be appreciated that the adjustable attachment of forearm support strap 18 to the mid-section of arm support envelope 12 is basically the same as that of shoulder strap 16 to arm support envelope 12.

The button portions of fasteners 24 are disposed adjacent each side of support strap 18 so that the sling can be used interchangeably for either the right or left arm of the wearer thereof.

Should shoulder strap 16 as disposed in FIG. 1 be uncomfortable for the wearer for reasons such as abrasions on the chest of a man, create undesirable pressure of the breast of a woman or for other reasons, then such strap can be connected to the rearmost fastener 24 and be disposed on the back of the shoulder and under the arm before connecting to the upper edge of envelope 12. Thus the same support is provided by strap 16 as shown in FIG. 1 but from the rear rather than the front of the wearer.

From the foregoing specification, it is obvious that the improved arm sling of the present invention presents an item that readily supports the wearer's arm in a clinically preferred manner. Further the improved arm sling of the present invention is lightweight, easy to use and economical to produce.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended Claims are intended to be embraced herein.

What is claimed is:

1. An improved arm sling for a wearer thereof comprising: an arm support envelope having an upper and lower portion and two end portions as disposed when the wearer thereof is in a generally upright position, one of said ends being disposed adjacent the elbow of said wearer and at least a portion of the upper edge adjoining said elbow and forearm of said wearer inside the cavity formed by said envelope; a first forearm portion in the form of a unitary shoulder strap secured to and extending from the upper elbow end portion of said envelope, over the shoulder and around the neck of the wearer thereof, and adjustably secured at its other end to the upper end portion of said envelope opposite said elbow end; and a second harness portion in the form of a disconnectable, length adjustable forearm strap slidingly attached at one end to the central portion of said shoulder strap and secured at its other end to the upper portion of said envelope generally midway its ends whereby a comfortable, well supported and yet simple to adorn and remove arm sling is provided.

2. The sling of claim 1 wherein the forearm strap length adjustable means is in the form of a sliding buckle.

3. The sling of claim 1 wherein the shoulder strap is length adjustable.

4. The sling of claim 3 wherein the length adjustable means for the shoulder strap is in the form of a slidable buckle.

5. The sling of claim 1 wherein the envelope is of such a length to extend beyond the hand of the wearer thereof whereby said hand is held in longitudinal alignment with the forearm of said wearer.

6. The sling of claim 1 wherein the shoulder strap connection to the end of the envelope opposite said elbow end is in the form of a pair of ring means, one secured to each side of said envelope with said strap passing therethrough whereby the upper portion of said envelope is pulled together by the weight of the arm of the wearer thereof within said envelope cavity.

7. The sling of claim 1 wherein the end of the forearm strap opposite its connection to the shoulder strap is connected to the upper portion of said envelope by means of a pair of rings, one secured to each side of said envelope with said forearm strap passing therethrough whereby the upper portion of said envelope is pulled together by the weight of the arm of the wearer thereof within said envelope cavity.

* * * * *